United States Patent
Smith

(10) Patent No.: US 7,422,014 B1
(45) Date of Patent: Sep. 9, 2008

(54) AIRFLOW MONITOR AND BREATHING DEVICE AND METHOD

(76) Inventor: Karen K. Smith, 3277 S. County Rd. 500 West, New Castle, IN (US) 47362

( * ) Notice: Subject to any disclaimer, the term of this patent is extended or adjusted under 35 U.S.C. 154(b) by 428 days.

(21) Appl. No.: 11/267,725

(22) Filed: Nov. 4, 2005

(51) Int. Cl.
*A61M 29/00* (2006.01)

(52) U.S. Cl. .............................. 128/204.23; 128/201.23

(58) Field of Classification Search ............ 128/204.23, 128/201.23; 600/481–486, 500–508, 529–538
See application file for complete search history.

(56) References Cited

U.S. PATENT DOCUMENTS

| | | | |
|---|---|---|---|
| D262,322 S | 12/1981 | Mizerak | |
| 5,535,739 A * | 7/1996 | Rapoport et al. | 128/204.23 |
| 5,704,345 A | 1/1998 | Berthon-Jones | |
| 5,797,852 A | 8/1998 | Karakasoglu et al. | |
| 6,142,950 A | 11/2000 | Allen et al. | |
| 6,213,955 B1 | 4/2001 | Karakasoglu et al. | |
| 6,290,654 B1 | 9/2001 | Karakasoglu | |
| 6,669,712 B1 * | 12/2003 | Cardoso | 606/199 |
| 7,114,497 B2 * | 10/2006 | Aylsworth et al. | 128/204.18 |
| 7,156,097 B2 * | 1/2007 | Cardoso | 128/206.11 |
| 2006/0169281 A1 * | 8/2006 | Aylsworth et al. | 128/204.23 |
| 2006/0174883 A1 * | 8/2006 | Aylsworth et al. | 128/204.21 |
| 2007/0093724 A1 * | 4/2007 | Nakano | 600/538 |

* cited by examiner

*Primary Examiner*—Steven O Douglas
(74) *Attorney, Agent, or Firm*—T.L. Garrett, PLC; Tanya L. Garrett

(57) ABSTRACT

An airflow monitor and breathing device having a flexible main band, an elongate main lead wire, and a nasal lead wire set, wherein the flexible main band, the main lead wire, and the nasal lead wire set cooperate to monitor the wearer's inspiration and expiration. An optional oral lead wire may be provided to extend down vertically from the nasal lead wire set towards the wearer's mouth. Also, an airflow breathing device having an airflow tube set, a flexible main band, and nasal tube set is provided to deliver a desired gas to a user.

17 Claims, 6 Drawing Sheets

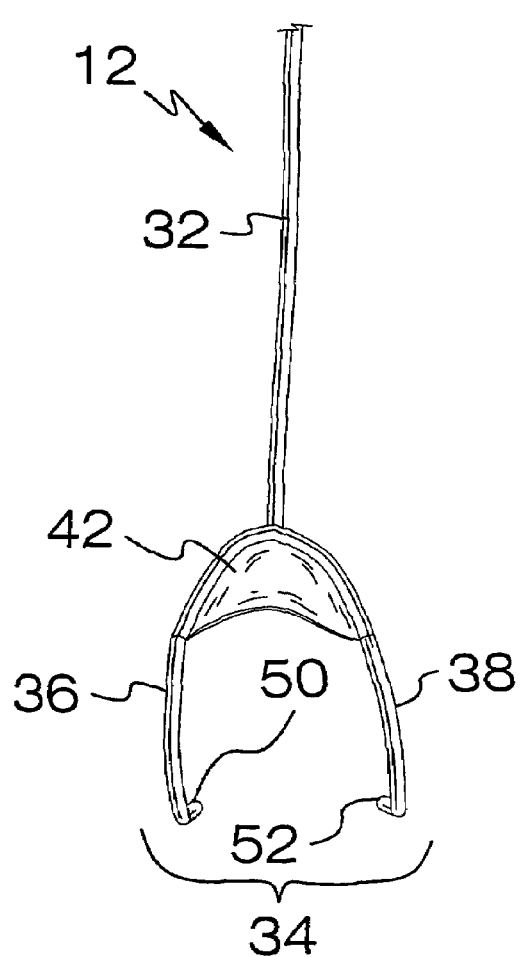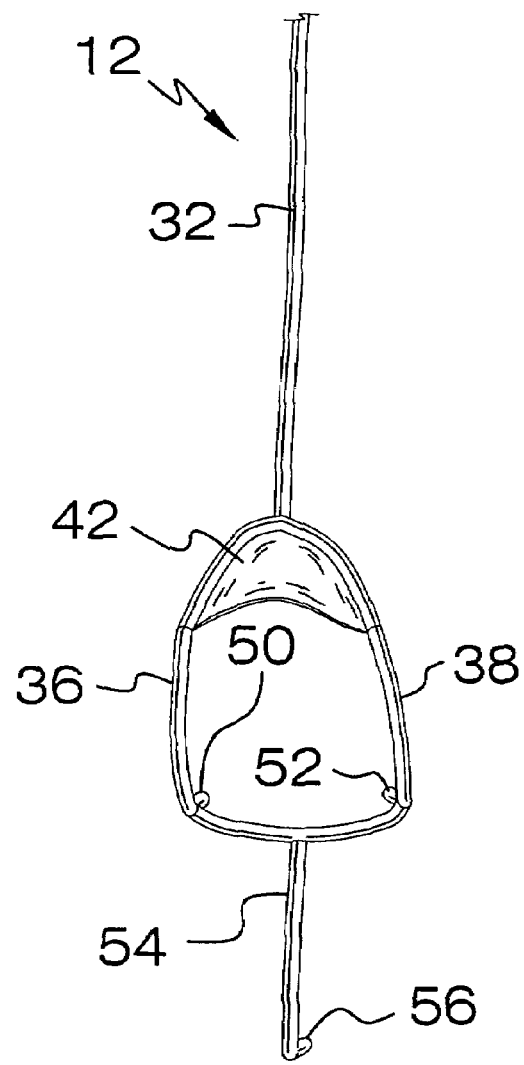
FIG. 3
FIG. 4

AIRFLOW MONITOR AND BREATHING DEVICE AND METHOD

FIELD OF THE INVENTION

The present invention generally relates to an airflow monitor and breathing device for use in the field of polysomonography.

BACKGROUND

The diagnosis of a patient's sleep disorders often involves the sleep analysis of the patient's sleep-related events, such as sleep disorder breathing. Such events are often analyzed by use of polysomnography (PSG), the monitoring and recording over an extended period of time of the temporal variations and the amplitude of the patients sleep-impacted, physiological parameters, including: heart rate, eye blink activity, upper respiratory airflow, thorax abdomen respiration efforts, the blood positive oxygen saturation level, electroencephalograms (EEG; electrical activity of the brain), electro-oculogram (EOG; electrical activity related to movement of the eyes), and the etromyograms (EMG; electrical activity of a muscle).

The use of devices and methods relating to monitoring a patient's sleep disorders and breathing patterns are disclosed in U.S. Pat. No. 6,213,955 issued in the name of Karakasoglu et al.

While existing devices suit their intended purpose, the need remains for a device and method that is easily applied to a user's face and also does not require multiple readjustments.

SUMMARY

In one aspect of the technology, an airflow monitor and breathing device is provided. Generally, the airflow monitoring and breathing device provides monitoring for respiratory air flow from the nostrils of the nose and/or the mouth of the face of a patient.

Additionally, the monitoring device may be used along or in combination with an oxygen delivering means.

In one aspect of technology, the airflow monitoring breathing device provides a flexible main band portion, an elongate main lead wire, and a nasal lead wire set, wherein the main lead wire, the flexible main band, and the nasal lead wire set cooperate to monitor the wearer's inspiration and expiration.

In another aspect of the technology, an optional oral lead wire is additionally provided.

Additionally, in another aspect of the technology, an airflow breathing device having an airflow tube set, a flexible main band, and a nasal tube set are provided.

A method of using the airflow monitor and breathing device is also provided.

BRIEF DESCRIPTION OF THE DRAWINGS

These and other objects, features and advantages of the present invention will become apparent from the following detailed description and the appended drawings in which:

FIG. 3 illustrates a front perspective view of a nasal version of an airflow monitor in accordance with one aspect of a technology.

FIG. 4 illustrates a front perspective view of a nasal/oral version of an airflow monitor in accordance with one aspect of a technology.

DETAILED DESCRIPTION OF THE INVENTION

The present invention generally relates to a device for monitoring respiratory airflow from the nostrils of the nose and/or the mouth of the face of a patient. The monitoring device may be used alone or in combination with an oxygen delivery means.

In general, the area of technology is directed to an airflow monitor used in the performance of polysommography for sleep apnea. More particularly, the airflow monitor is applied to a user's face by taping a main band at the bridge of a user's nose and then by positioning sensor wires in front of each nostril. The wiring extends from the main band upwardly over the forehead to a bundle of wires at the top of the user's head, wherein the bundle of wires may be any desired monitoring leads that have come or may come into existence such as, but not limited to a plurality of EEG, EOG, and EMG leads.

The present area of technology allows for improved tracings with air movement inspiration and expiration. Additionally, the area of technology provides enhanced comfort for a patient using the technology. Additionally, the present area of technology provides an aspect having a nasal version and another aspect having a nasal/oral version, both of which will be applied to a user in a similar manner. The present area of technology provides an airflow monitor for use during testing for sleep apnea and related sleep disorders. Additionally, the present area of technology provides an airflow breathing device to assist in the breathing process. The area of technology does not require multiple adjustments or multiple adhesive for use in the monitoring process.

The airflow monitor and breathing device may communicate with any suitable PSG device as will be appreciated by a skilled artisan to facilitate the monitoring and diagnosis of a patient's sleep disorders. The present area of technology eliminates the need for sensor wires to extend to and be retained by a patient's ears. This provides a patient wearing the device a greater freedom of movement and eliminates the need for readjusting wires when a patient lying horizontally rolls over while wearing the device.

Figure 1:
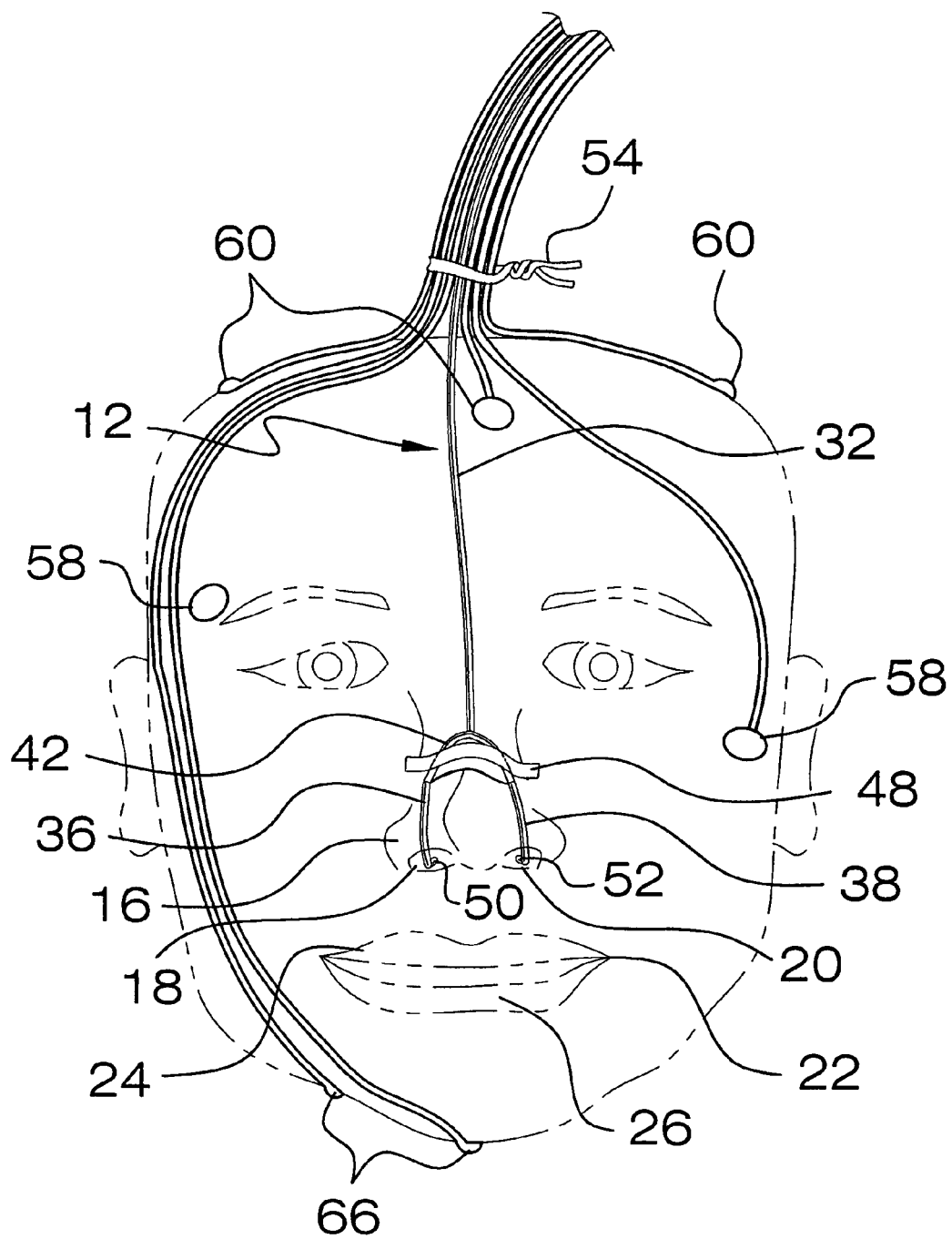
FIG. 1 illustrates a first elevational view of a nasal version of an airflow monitor applied to a user's face in accordance with one aspect of the technology.

Referring now to the drawings, in particular, FIG. 1 illustrates a front elevational view of an airflow monitor incorporating the present area of technology mounted on the face of a human being. FIG. 1 illustrates use of an airflow monitor 12 for breath monitoring and airflow monitoring used on a patient in the form of a human being having a head 14 having a centrally disposed nose 16 with first and second nostrils 18 and 20 which open downwardly towards a mouth 22 formed by upper and lower lips 24 and 26. As shown, the upper lip 24 is positioned below the nostrils 18 and 20.

The airflow monitor 12 provides a main lead wire 32, a flexible main band 42, and a nasal lead wire set 34. The main lead wire 32, the flexible main band portion 42, and the nasal lead wire set 34 are in electrical communication with each other and cooperate to monitor a wearer's inspiration and expiration. The main lead wire 32 is an elongate wire, which is generally disposed in a vertical position on a user's face 30 extending upwardly from the flexible main band portion to a wearer's scalp. The flexible main band 42 is flexibly configured to conform to the nose 16. The flexible band 42 portion may be positioned on a bridge portion of the nose and has associated air exchange sensors (not shown) disposed thereon such as, but not limited to thermisters that operate to monitor or sense an exchange of air as a patient wearing the airflow monitor 12 respirates. However, any suitable air exchange sensors may be used that have come or may come into existence to monitor or sense an exchange of air. Additionally, the air exchange sensors may be removably or alternatively, integrally formed with the flexible main band 42.

The nasal lead wire set 34 has a first nasal lead wire 36 and a second nasal lead wire 38 that extend downwardly toward the mouth 22 in a wye arrangement from the main lead wire 32. The first nasal lead wire 36 and the second nasal lead wire 38 are spaced apart in an arrangement that allows the first lead wire 36 to extend to the first nostril 18 and the second lead wire 38 to extend to the second nostril 20.

In another aspect of the area of technology, shown in FIGS. 1 and 3, an optional pair of nasal airflow monitor sensors 50 and 52 are provided at the end of the first nasal lead wire 36 and the second nasal lead wire 38, respectively. The sensors 50, 52 may be in the form of nasal tips as shown in FIG. 3. Alternatively, the nasal sensors may be integrally formed with the first and second nasal lead wire 36, 38 and may be located on a portion of each lead wire 36, 38 such that when each lead wire is bent in a suitable position below or near each nostril, the sensors operate to sense inspiration and expiration of the patient wearing the airflow monitor 12.

Figure 5:
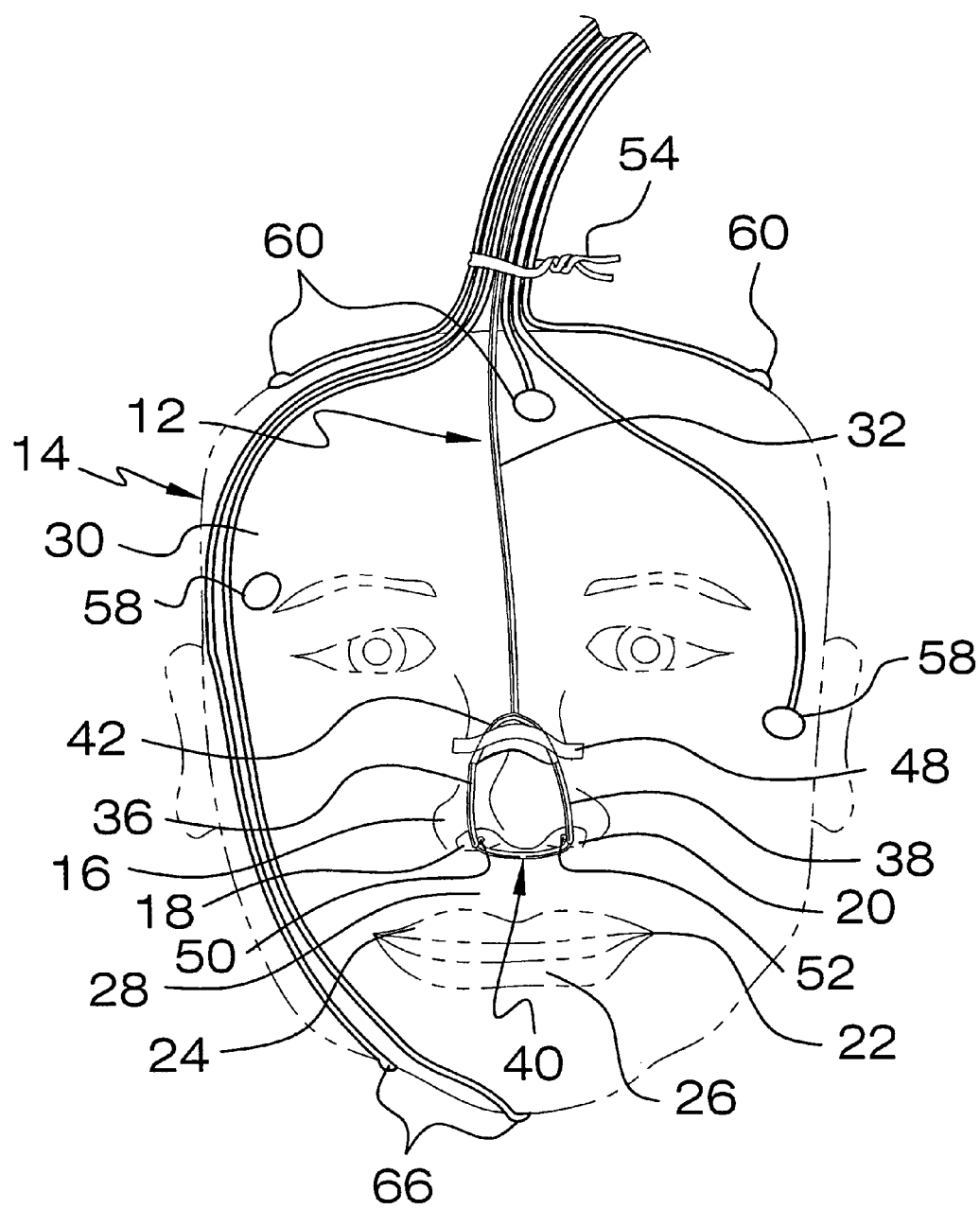
FIG. 5 illustrates a front elevation view of a nasal version of an airflow monitor applied to a user's face in accordance with one aspect of a technology.

In another aspect of the technology, the nasal lead wires 36, 38 may be integrally or separately formed to form a loop extending in a horizontal arrangement under the first and second nostrils 18, 20 as shown in FIG. 5. When lead wires 36, 38 are integrally formed, they form one lead wire 40. Alternatively, when the lead wires are separately formed, they may be connected by an optional intermediary wire disposed between the ends of each lead wire 36, 38.

Figure 2:
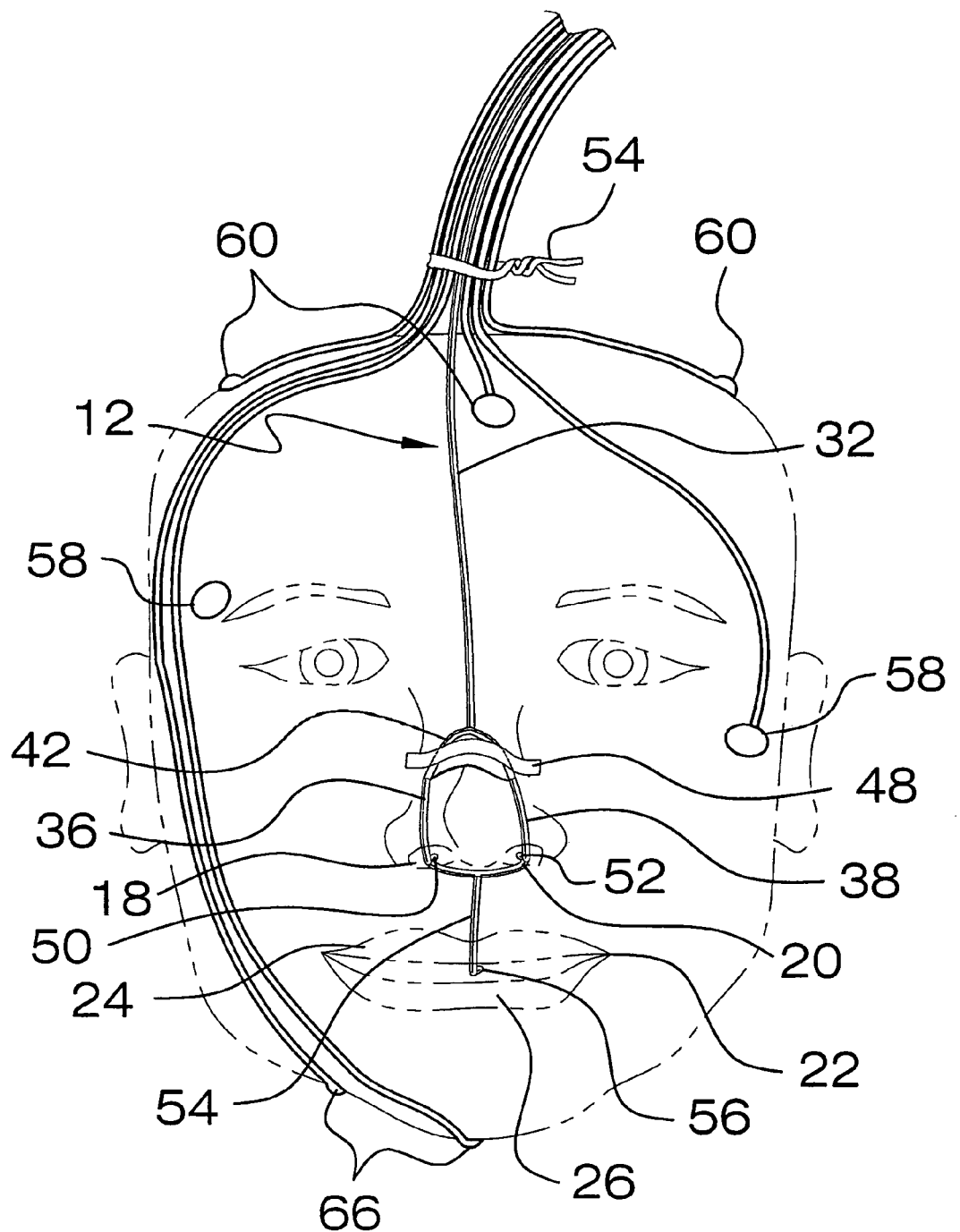
FIG. 2 illustrates a front elevational view of a nasal/oral version of an airflow monitor applied to a user's face in accordance with one aspect of the technology.

FIG. 2 illustrates another aspect of the present area of technology. FIG. 2 illustrates a front elevational view of an airflow monitor incorporating the present area of technology mounted on the face of a human being. FIG. 4 illustrates a perspective of the airflow monitoring device As shown in more detail in FIG. 4, an optional oral lead wire 54 extends from the first nasal sensor 50 and the second nasal sensor 52, respectively, in a substantially tee-shaped arrangement and further extends in a vertical position downwardly toward the mouth 22 and then is positioned in a location between the upper lip 24 and the lower lip 26. The oral lead wire 54 further has an oral sensor 56 for monitoring oral airflow. The oral airflow monitor lead wire portion 54 and sensor 56 may be removably formed or alternatively, may be permanently formed with the nasal lead wire set 36 and 38, respectively, to form a closed loop as shown in more detail in FIG. 4.

As shown in FIGS. 1-2, and 5, a plurality of other monitoring leads are provided. The monitoring leads may be, but are not limited to a plurality of EEG leads 60 as shown positioned on a top portion of a user's scalp, a plurality of EOG 58 leads positioned near a patient's eye, and a plurality of EMG leads 66 positioned near or on a patient 10. The leads 32, 58, 60, and 66, respectively may be gathered as a bundle 62 and may be held together by any suitable holding means that have or may come into existence such as, but not limited to a strap or a tie 54 on top of a patient's head.

Each of the plurality of leads are then attached to or communicate signals with an associated PSG device will known in the PSG arts. Such a device may be a acoustic device as disclosed in U.S. Pat. No. 6,213,955 issued in the name of Karakasoglu et al., or apnea screening and detection devices disclosed in U.S. Pat. No. 6,290,654 issued in the name of Karakasoglu, and U.S. Pat. No. 6,142,950 issued in the name of Allen et al. However, any device that has come or may come into existence that may be used in the PSG art to monitor inspiration and respiration.

The airflow monitor 12 may be made of flexible wiring that may be bent to adjust in conformance to a user's face both above the nostrils and in an area between the nostrils and the mouth. In one aspect of the area of technology, the flexible wiring may also be adjusted to extend to a user's mouth. Additionally, the airflow monitor may be made with or coated with a rubber material or any other material that has come or may have come into existence that is suitable for use with wiring known in the field of PSG monitoring arts.

In an aspect of the technology, an optional piece or pieces of adhesive tape 48 may be used to secure the main band portion 42 to a user's face 30. Alternatively, an adhesive may be applied to a rearward portion of the flexible main band to removably adhere the flexible main band to the face 30.

Additionally, an optional cannula may be provided for use in combination with the airflow monitor and may be positioned under a patient's nostrils to deliver desired gases, such as oxygen to a patient.

Figure 6:
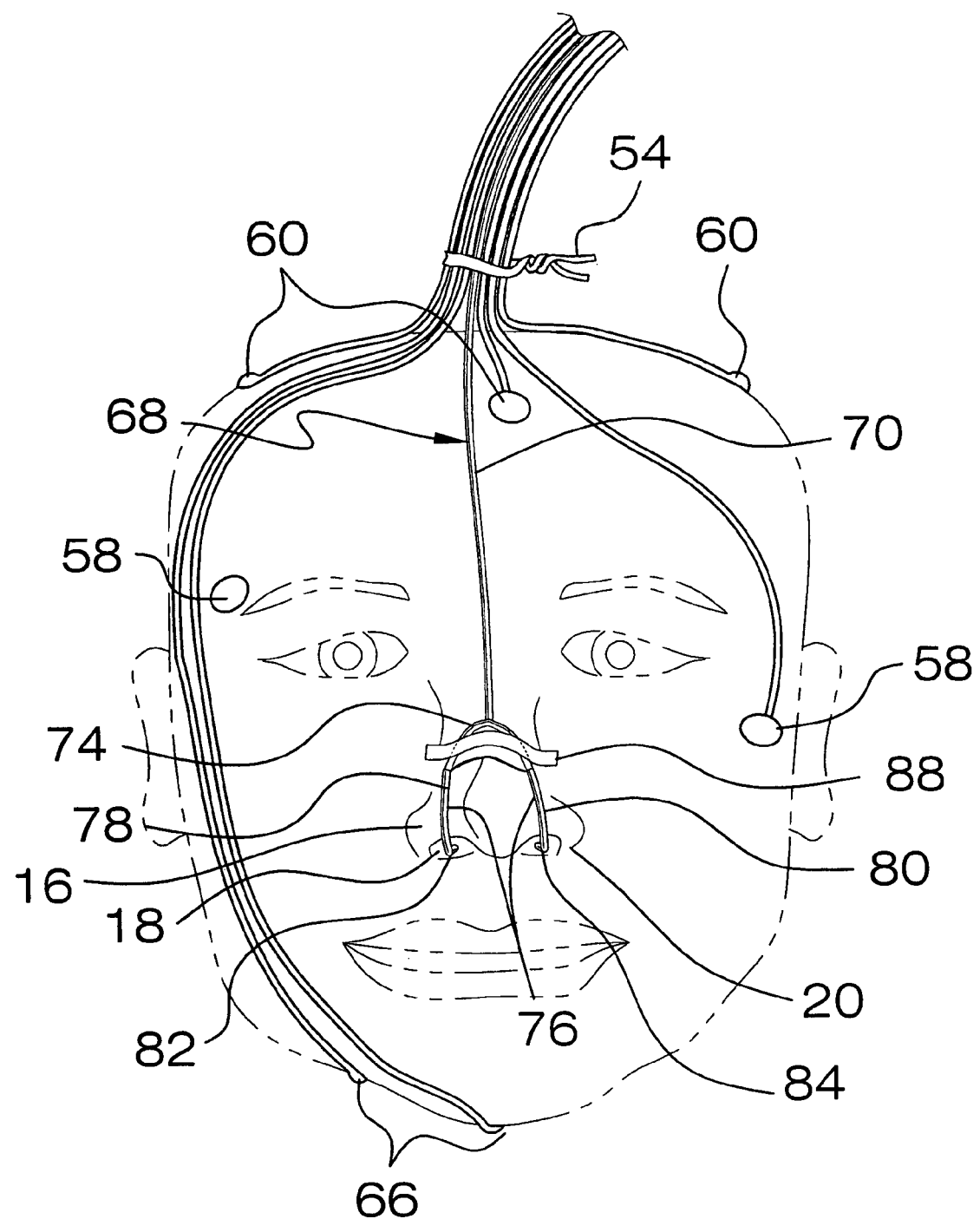
FIG. 6 illustrates a front elevation view of an airflow breathing device having an oxygen tube set in accordance with one aspect of the technology.

In aspects of the technology as shown in FIG. 6, an airflow breathing device that may operate alone or in combination with the airflow monitor 12, shown in FIGS. 1-5. Referring now to the drawings, FIG. 6 illustrates a front elevational view of an airflow-breathing device incorporating the present area of technology mounted on the face of a human being. For illustrative purposes, the numbering of the parts of the human being's face will be numbered in the same manner as described with regard to FIGS. 1-5 above.

More particularly, the airflow-breathing device 68 has an elongate main tube 72, which is generally disposed in a vertical position on a user's face 30 as herein described. The airflow breathing device 68 further has a flexible main band 74 flexibly configured to conform to the nose 16, and a nasal tube set 76 having a first nasal tube 78 and a second nasal tube 80 that extends downwardly from the bridge of the nose towards the mouth 22 in a wye arrangement from the main tube 72. The elongate main tube 72 and the nasal tube set 76 are in fluid communication to deliver a desired gas, such as oxygen to a user. The first nasal tube 78 and the second nasal tube 80 are spaced apart in an arrangement that allows the first nasal tube 78 to extend to the first nostril 18 and the second nostril tube 80 to extend to the second nostril 20.

Additionally, a pair of nasal airflow ports 82 and 84 may be provided at the end of the first nasal tube 78 and the second nasal tube 80, respectively, to facilitate delivery of gases such as oxygen to a patient's nose.

Also, a piece or pieces of tape 88 may be adhered to the flexible main band and face to secure the band 74 to the face. Alternatively, adhesive adhered to a rear portion of the flexible band 74 may be adhered to the face 30 in a similar manner as described with reference to FIGS. 1-5 herein.

Figure 7:
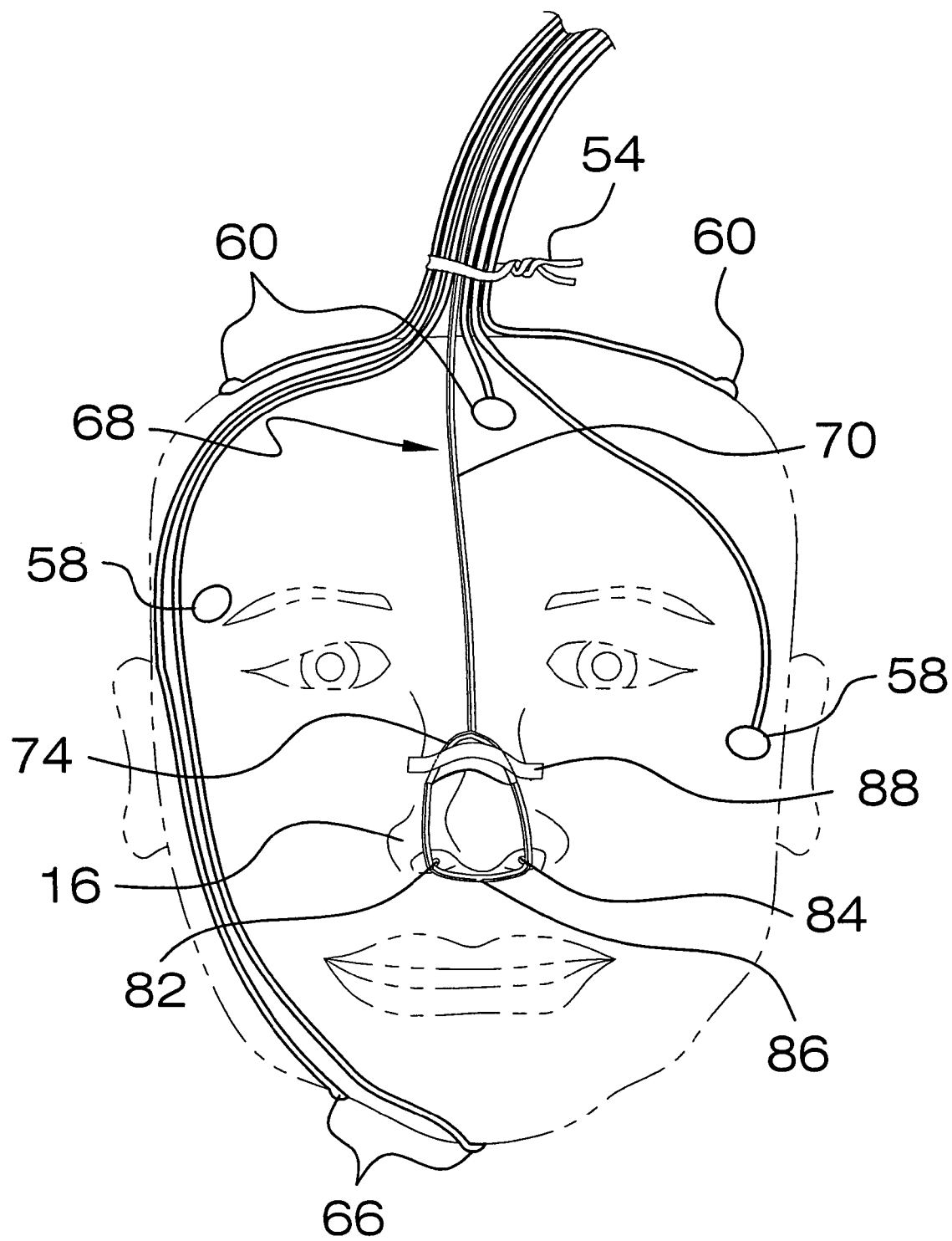
FIG. 7 illustrates a front elevation view of an airflow breathing device having an oxygen tube looped beneath a user's nostrils to deliver a desired gas to a user in accordance with one aspect of the technology.

Additionally, in another aspect of the technology as shown in FIG. 7, an optional tube 86 may be integrally formed between the ports 82 and 84 to provide a continuous flow of air or oxygen flow through the airflow-breathing device 68.

In operation, the airflow monitoring and breathing device may be adhered to a user's face by positioning the main band on a user's nose and then by positioning the nasal lead wire set under the patient's nose in order to sense an exchange of air. If the oral version is used, then the mouth portion having the oral sensor may be suitably arranged between the upper and lower lip. If additional oxygen is needed, then an oxygen cannula may also be provided for the patient's use.

Alternatively, the breathing device 68 may be used alone or in combination with the airflow monitor to deliver oxygen to the patient and may be applied to a patient's face in a similar manner as described with respect to the airflow monitor.

A skilled artisan will appreciate that the foregoing examples are illustrative only, and not limitative of the scope of the technology.

From the foregoing, it should be appreciated that several airflow monitoring and breathing devices, and their methods of use have been provided.

While several aspects have been presented in the foregoing detailed description, it should be understood that a vast number of variations exist and these aspects are merely an example, and it is not intended to limit the scope, applicability or configuration of the invention in any way. Rather, the foregoing detailed description provides those of ordinary skill in the art with a convenient guide for implementing a desired aspect of the invention and various changes can be made in the function and arrangements of the aspects of the technology without departing from the spirit and scope of the appended claims.

What is claimed is:

1. An airflow monitor and breathing device comprising:
   a flexible main band flexibly configured to conform to a human nose;
   an elongate main lead wire that in operation is disposed in a vertical position on a user's face extending upwardly from the flexible main band to a user's scalp; and
   a nasal lead wire set that in operation extends downwardly from a main lead wire towards a user's mouth, the nasal lead wire set is in electrical communication with the nasal lead wire set and flexible main band, wherein the main lead wire, the flexible main band and the nasal lead wire set cooperate to monitor a wearer's inspiration and expiration.

2. The device of claim 1, wherein the flexible main band is positioned on a bridge portion of the nose and comprises:
   associated air exchange sensors disposed thereon.

3. The device of claim 2, wherein the air exchange sensors comprise thermisters that operate to monitor or sense an exchange of air as a patient wearing the airflow monitor respirates.

4. The device of claim 2, wherein the air exchange sensors are removably formed with the flexible main band.

5. The device of claim 2, wherein the air exchange sensors are integrally formed with the flexible main band.

6. The device of claim 1, wherein the nasal lead wire set comprises:
   a first nasal lead wire; and
   a second nasal lead wire,
   wherein the first and second nasal lead wire extend downwardly from the main lead wire toward a human mouth in a wye arrangement from the main lead wire, and wherein the first nasal lead wire and the second nasal lead wire are spaced apart such that the first lead wire extends to a first nostril and the second lead wire extends to a second nostril.

7. The device of claim 6, further comprising:
   a first nasal airflow monitor sensor associated with the first nasal lead wire; and
   a second nasal airflow monitor sensor associated with the second nasal lead wire.

8. The device of claim 7, wherein the first and second nasal airflow sensors further comprise nasal tips.

9. The device of claim 7, wherein the first and second nasal airflow sensors are integrally formed with the first and second nasal lead wire, respectively.

10. The device of claim 6, wherein the nasal lead wires cooperate to form a loop extending horizontally under the first and second nostrils.

11. The device of claim 10, wherein the nasal lead wires are severably formed and further comprise:
    an intermediary wire disposed between a respective end of each of the nasal lead wires.

12. The device of claim 1, further comprising:
    an oral lead wire extending from the first nasal sensor and the second nasal sensor, respectively, in a substantially tee-shaped arrangement, wherein the oral lead wire further extends in a vertical position downwardly toward the mouth and is positioned in a location between an upper lip and a lower lip, the oral lead wire comprising an oral sensor that operates to monitor oral airflow.

13. The device of claim 12, wherein the oral airflow monitor lead wire and oral sensor are both removably formed with the nasal lead wire set.

14. The device of claim 12, wherein the oral airflow monitor lead wire and the oral sensor are both integrally formed with the nasal lead wire set.

15. The device of claim 1, wherein the main lead wire is bundled with a plurality of other polysomnography monitoring leads selected from at least one of an electroencephalogram lead, an elecro-oculogram lead, and an etromyogram lead.

16. The device of claim 1, wherein the main lead wire, and the nasal wire set comprise:
    flexible wiring that bends to adjust in conformance to a user's face both above the nostrils and in an area between the nostrils and the mouth, and wherein the flexible wiring further comprises a rubber coating.

17. The device of claim 1, wherein the flexible main band is adhered to the face using adhesive tape.

* * * * *

UNITED STATES PATENT AND TRADEMARK OFFICE
CERTIFICATE OF CORRECTION

| | | |
|---|---|---|
| PATENT NO. | : 7,422,014 B1 | Page 1 of 1 |
| APPLICATION NO. | : 11/267725 | |
| DATED | : September 9, 2008 | |
| INVENTOR(S) | : Karen K. Smith | |

It is certified that error appears in the above-identified patent and that said Letters Patent is hereby corrected as shown below:

In the drawings, sheet 2, Fig. 2, the reference number 54 to an optional oral lead wire should be changed to the corrected reference number 54(a) to an optional oral lead wire as is cited in the specification in Col. 3 Ln. 51:

In the drawings, sheet 2, Fig. 2, the reference number 54 to a strap or tie should be changed to the corrected reference number 54(b) to a strap or tie as is cited in the specification in Col. 4, Ln. 4:

Col. 1, Ln. 13, the words --, such as-- should be changed to --, such as,-- to correct a grammatical error:

Col. 3, Ln. 51, an optional oral lead wire with reference number --54-- should be changed to the corrected an optional oral lead wire with reference number --54(a)--:

Col. 4, Ln. 4, a strap or tie with reference number --54-- should be changed to the corrected a strap or tie with reference number --54(b)--:

Col. 4, Ln. 6, the word --will-- should be changed to --well-- to correct a spelling error.

Col. 4, Lns. 44 and 51, the reference number --72-- to an elongated main tube should be changed to the correct reference number --70-- to an elongated main tube:

Signed and Sealed this

Twenty-second Day of September, 2009

David J. Kappos
*Director of the United States Patent and Trademark Office*